United States Patent
Koshti et al.

(10) Patent No.: US 7,205,436 B2
(45) Date of Patent: *Apr. 17, 2007

(54) PROCESS FOR MANUFACTURE OF QUATERNARY AMMONIUM TOSYLATE SALTS OF CINNAMIDOALKYLAMINES AND / OR BENZAMIDOALKYLAMINES

(75) Inventors: Nirmal Madhukar Koshti, Mumbai (IN); Shubhangi Dattaram Naik, Thane (West) (IN); Bharat Bhikaji Parab, Mumbai (IN); Tanaji Shamrao Jadhav, Navi Mumbai (IN); Subhash Shivling Nashte, Navi Mumbai (IN)

(73) Assignee: Galaxy Surfactants Limited, Maharashtra (IN)

( * ) Notice: Subject to any disclaimer, the term of this patent is extended or adjusted under 35 U.S.C. 154(b) by 12 days.

This patent is subject to a terminal disclaimer.

(21) Appl. No.: 11/128,980

(22) Filed: May 13, 2005

(65) Prior Publication Data
US 2005/0209327 A1 Sep. 22, 2005

Related U.S. Application Data

(62) Division of application No. 10/682,004, filed on Oct. 8, 2003, now Pat. No. 7,045,139.

(51) Int. Cl.
*C07C 233/00* (2006.01)
(52) U.S. Cl. .................. 564/157; 564/134; 564/142
(58) Field of Classification Search ................ 514/554; 562/45; 564/157, 134, 142
See application file for complete search history.

(56) References Cited

U.S. PATENT DOCUMENTS

| 5,427,773 | A | * | 6/1995 | Chaudhuri et al. | ........... 424/60 |
| 5,451,394 | A | | 9/1995 | Chaudhuri et al. | |
| 6,426,435 | B1 | * | 7/2002 | Koshti et al. | ............... 564/157 |
| 6,613,340 | B2 | | 9/2003 | Koshti et al. | |

OTHER PUBLICATIONS

Jachowicz et al., Photodegredation of hair and its Photoprotection by a substantive Photofilter, Drug and Cosmetic Industry, (1995), 157 (6), 28, 30, 32, 35-6, 38, 40, 42, 44.

Anselmi et al., Conformation and Dynamics in a Solution of an N-Quatermized Cinnamide Derivative: a molecule active as a UV filter, Magnetic Resonance in Chemistry (1992), 30 (10), 944-9.

* cited by examiner

*Primary Examiner*—Thurman K. Page
*Assistant Examiner*—Chukwuma Nwaonicha
(74) *Attorney, Agent, or Firm*—Merchant & Gould P.C.

(57) ABSTRACT

An efficient, simple, high yielding, eco-friendly process for the manufacture of tosylates quaternary ammonium salts of cinnamidoalkylamines and/or benzamidoalkylamines (Formula I) has been described. These compounds are substantive UV-absorbers. They are useful in making fabric care products and personal care products.

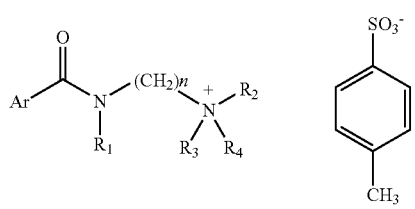

I

The scope of this methodology has been demonstrated by converting water soluble organic sunscreen quaternary halides to their corresponding tosylates of Formula VI.

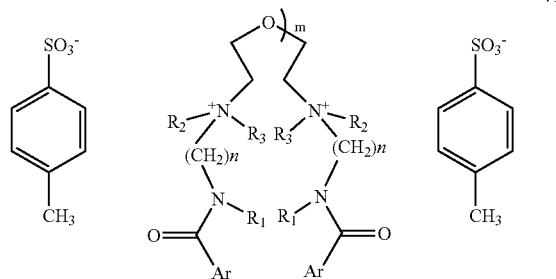

VI

2 Claims, No Drawings

PROCESS FOR MANUFACTURE OF QUATERNARY AMMONIUM TOSYLATE SALTS OF CINNAMIDOALKYLAMINES AND / OR BENZAMIDOALKYLAMINES

This application is a division of U.S. application Ser. No. 10/682,004 filed on Oct. 8, 2003 now U.S. Pat. No. 7,045,139. Such application is incorporated herein by reference.

FIELD OF INVENTION

This invention relates to a novel process for manufacture of cationic, quaternary ammonium tosylate salts of cinnamidoalkylamines and/or benzamidoalkylamines of Formula I. This invention particularly relates to the synthesis of non-hydrolyzable, non-irritating UV-absorbers having substantivity to cotton, wool, skin and hair.

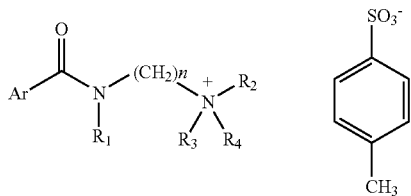

Formula I

ArCO is selected from p-N,N-dimethylamino benzoyl and/or p-methoxy cinnamoyl;

$R_1$ is selected from H or alkyl groups containing from 1 to 6 carbon atoms;

$R_2$ and $R_3$ are independently selected from alkyl groups containing from 1 to 12 carbon atoms;

$R_4$ is selected from alkyl or alkenyl groups containing from 8 to 22 carbons; and n is an integer having values from 1 to 6.

BACKGROUND AND PRIOR ART

Quaternised UV-absorbers with tosylate anion are of significance for their substantivity to skin and hair as well as their mildness compared to the corresponding quaternary halides [Soap, Perfumery & Cosmetics, 29–34, March 1997].

U.S. Pat. No. 4,680,144 (1987) and U.S. Pat. No. 5,427,773 (1995) disclose preparations of these kind of cationic substantive photofilters like dodecyl dimethyl amino benzamido propyl dimethyl ammonium tosylate. In this process, a primary amino group of N,N-dimethyl propyl diamine is reacted with dimethyl amino benzoic acid to form an amidoamine and then the tertiary amino group of the amidoamine is quaternised with alkyl tosylate. Similarly, U.S. Pat. No. 6,613,340 (2003) discloses cationic tosylate salts from cinnamidoalkylamines following the same methodology. The procedures described in these patents are very tedious where alkyl tosylates that are used for quaternisation are in turn prepared from fatty alcohols and tosyl chloride. This tosylation reaction is done in a suitable solvent using stoichiometric quantities of tertiary amine bases like triethylamine or pyridine. The organic bases mop up the hydrochloric acid generated and the subsequent hydrochloride-base salt that is formed as a by-product has to be removed by washing the reaction mixture with water. This significantly increases the effluent load. Another disadvantage of this process from prior art is that the reaction for preparation of alkyl tosylates is carried out in either halogenated solvents like dichloromethane or aromatic solvents. Purification of alkyl tosylate also results in significant loss of yield and simultaneous increase in effluent treatment. This purification step is necessary due to the presence of unconverted fatty alcohols in alkyl tosylates. The quaternisation of cinnamidoalkylamines and/or benzamidoalkylamines with alkyl tosylate does not give quantitative conversion and hence after the purification step isolated yields of quaternised UV-absorbers range between 65 to 70% only.

In summary, all these factors make the process for making quaternised UV-absorbing tosylates not only tedious and expensive but also non-environment friendly. Hence, there is a need for a simple, quantitative and eco-friendly process for making these substantive UV-absorbers that are superior to the corresponding halides due to tosylate as counter ion.

SUMMARY OF THE INVENTION

The present invention provides a novel, efficient, high yielding and environmental friendly process for preparing quaternary ammonium tosylate salts of cinnamidoalkylamines and/or benzamidoalkylamines of Formula I, wherein;

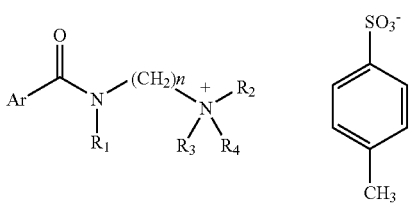

I

ArCO is selected from p-N,N-dimethylamino benzoyl and/or p-methoxy cinnamoyl;

$R_1$ is selected from H or alkyl groups containing from 1 to 6 carbon atoms;

$R_2$ and $R_3$ are independently selected from alkyl groups containing from 1 to 12 carbon atoms;

$R_4$ is selected from alkyl or alkenyl groups containing from 8 to 22 carbons; and n is an integer having values from 1 to 6, the process comprising the steps of i) quaternisation of 1.0 mole of cinnamidoalkylamine and/or benzamidoalkylamine of Formula II with 1.0 mole of alkylating compound of Formula III, wherein, $R_1$, $R_2$, $R_3$, $R_4$ and n is same as that in the compound of said Formula I, with or without solvent, to obtain a quaternary ammonium halide of Formula IV;

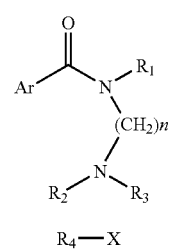

II

III

-continued

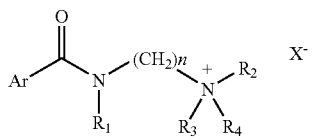

IV (ii) treating the aqueous solution of quaternary ammonium halide of Formula IV obtained in step (i) with stoichiometric quantity of sodium p-toluene sulphonate to get water insoluble quaternary ammonium tosylate of Formula I.

The methodology described in the present invention is generally useful for converting water-soluble quaternary organic sunscreen ammonium halides (Formula V) to water insoluble quaternary sunscreen ammonium tosylates (Formula VI).

DETAILED DESCRIPTION OF THE INVENTION

The process of making compounds of Formula I described in the present invention comprises of two steps, a) synthesis of quaternary ammonium halides of Formula IV and b) conversion of water-soluble quaternary ammonium halides of Formula IV to water-insoluble quaternary ammonium tosylates of Formula I.

A) Synthesis of Quaternary Ammonium Halides of Formula IV.

The UV-absorbing ciniamidoalkylamines and/or benzamidoalkylamines of Formula II are synthesised as per the literature procedures [U.S. Pat. No. 5,427,773 (1995), U.S. Pat. No. 6,613,340 (2003)]. These amidoamines are quaternised using commercially available alkyl halides of Formula III in aqueous/alcoholic medium to give quantitative generation of corresponding water-soluble, UV-absorbing, quaternary ammonium halides of Formula IV.

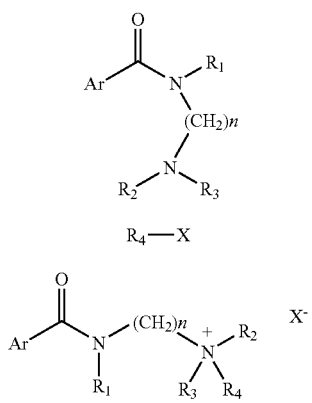

The quaternisation reaction can be conveniently done in a pressure reactor as well as in an open system. The temperatures suitable for pressure reaction range from about 100–135° C. with the pressures up to 50 psi. The choice of solvent generally dictates reaction conditions including selection of closed reactor or open vessel. Water as a solvent and a pressure reactor are the most preferred conditions since the subsequent step is done in aqueous medium. Any other polar solvent may be used for quaternisation, however, in that case solvent has to be removed and replaced by water for second step. The progress of the quaternisation reaction is monitored by measuring the amount of unreacted alkylating agent by chromatography or by estimation of unquaternized amidoamine or by estimation of $X^-$, the halide anion.

Alternately, quaternisations can be carried out by directly reacting cinnamidoalkylamines and/or benzamidoalkylamines of Formula II with alkyl halides of Formula III at from about 100 to 140° C. for 4 to 24 hours without any solvent and in an inert atmosphere of nitrogen. The progress of the reaction is monitored by estimation of unquaternised tertiary amine as well as by the estimation of liberated halide.

b) Conversion of Water Soluble Quaternary Compounds of Formula IV to Water-insoluble Quaternary Ammonium Tosylates.

The aqueous solution (30%) of quaternary sunscreen ammonium halides of Formula IV of step (i) is then treated with equimolar quantities of sodium p-toluene sulphonate at room temperature. This results in quantitative precipitation of corresponding tosylates of Formula I. The precipitates are then washed off with copious amount of water and dried under vacuum to give quaternary sunscreen ammonium tosylates of Formula I.

In another embodiment, the process of the present invention relates to manufacture of quaternary ammonium tosylates of Formula I, in which ArCO is selected from p-N,N-dimethylamino benzoyl and/or p-methoxy cinnamoyl; $R_1$ is selected from H or alkyl groups containing from 1 to 6 carbon atoms, $R_2$ and $R_3$ are independently selected from alkyl groups containing from 1 to 12 carbon atoms; $R_4$ is selected from alkyl or alkenyl groups containing from 8 to 22 carbons; n is an integer having values from 1 to 6; from the compounds of Formula II, III, IV and sodium p-toluene sulphonate, with respective substituents ArCO, $R_1$, $R_2$, $R_3$, and n of Formula II, $R_4$ of Formula III and ArCO, $R_1$, $R_2$, $R_3$, $R_4$, and n of Formula IV as defined for the compounds of Formula I in this embodiment.

In another embodiment, the process of the present invention relates to manufacture of a quaternary ammonium tosylate of Formula I, in which ArCO=p-methoxy cinnamoyl, $R_1$=H, $R_2$, $R_3$=—$CH_3$, $R_4$=—$C_{12}H_{25}$ and n=3, from the compound of Formula II (p-methoxy cinnamidopropyl dimethylamine, ArCO=p-methoxy cinnamoyl, $R_1$=H, $R_2$, $R_3$=—$CH_3$, n=3) quaternised with compound of Formula III (lauryl chloride, $R_4$=—$C_{12}H_{25}$, $X^-$=chloride anion) forming the quaternised compound of Formula IV (p-methoxy cinnamidopropyl dimethyl lauryl ammonium chloride, $R_1$=H, $R_2$, $R_3$=—$CH_3$, $R_4$=—$C_{12}H_{25}$, n=3, $X^-$=chloride anion), aqueous solution of which is then treated with stoichiometric quantity of sodium p-toluene sulphonate.

In another embodiment, the process of the present invention relates to manufacture of a quaternary ammonium tosylate of Formula I, in which ArCO=p-N,N-dimethylamino benzoyl, $R_1$=H, $R_2$, $R_3$=—$CH_3$, $R_4$=—$C_{12}H_{25}$ and n=3, from the compound of Formula II (p-N,N-dimethylamino benzamidopropyldimethylamine, ArCO=p-N,N-dimethyl aminobenzoyl, $R_1$=H, $R_2$, $R_3$=—$CH_3$, n=3) quaternised with compound of Formula III (lauryl chloride, $R_4$=—

$C_{12}H_{25}$, $X^-$=chloride anion) forming the quaternised compound of Formula IV (p-N,N-dimethylamino benzamido propyldimethyllauryl ammonium chloride, $R_1$=H, $R_2$, $R_3$=—$CH_3$, $R_4$=—$C_{12}H_{25}$, n=3, $X^-$=chloride anion), aqueous solution of which is then treated with stoichiometric quantity of sodium p-toluene sulphonate.

This methodology is extended to a general procedure for converting water-soluble quaternary sunscreen ammonium halides to water insoluble quaternary sunscreen ammonium tosylates. This is demonstrated by using water soluble bis quaternary UV-absorber of U.S. Pat. No. 6,426,435 (2002).

In another embodiment, isopropanolic solution of quaternary sunscreen ammonium bis-chloride of Formula V is treated with two equivalence of sodium tosylate 80° C. for 8 hours. The separated sodium chloride is filtered to give alcoholic solution of bis-quaternary sunscreen ammonium tosylates of Formula VI.

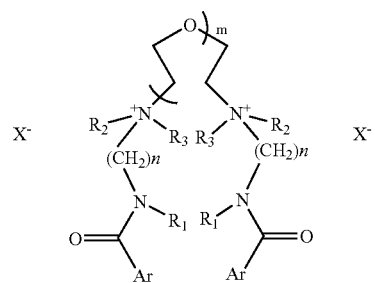

V

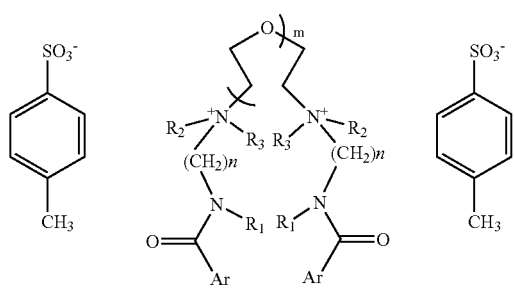

VI

In yet another embodiment, the process of the present invention relates to manufacture of a quaternary ammonium tosylate of Formula VI, in which ArCO is selected from p-N,N-dimethylamino benzoyl and/or p-methoxy cinnamoyl; $R_1$ is selected from H or alkyl groups containing from 1 to 6 carbon atoms, $R_2$ and $R_3$ are independently selected from alkyl groups containing from 1 to 12 carbon atoms; n is an integer having values from 1 to 6; m is an integer having values from 1 to 10; from the compounds of Formula V and sodium p-toluene sulphonate, with respective substituents ArCO, $R_1$, $R_2$, $R_3$, n and m of Formula V, as defined for the compounds of Formula VI.

In yet another embodiment, the present invention relates to a water insoluble quaternary ammonium bis tosylates of Formula VI;

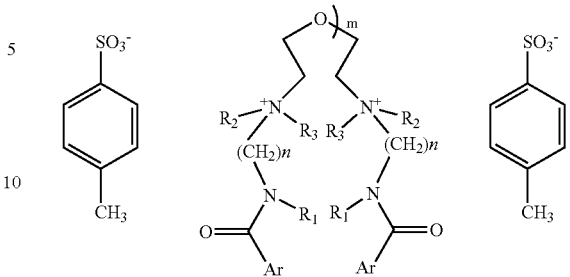

VI where; ArCO is selected from p-N,N-dimethylamino benzoyl and/or p-methoxy cinnamoyl;

$R_1$ is selected from H or alkyl groups containing from 1 to 6 carbon atoms;

$R_2$ and $R_3$ are independently selected from alkyl groups containing from 1 to 12 carbon atoms;

n is an integer having values from 1 to 6; and m is an integer having values from 1 to 10.

The processes described for quaternised UV-absorbing tosylate salts in U.S. Pat. No. 4,680,144 (1987), U.S. Pat. No. 5,427,773 (1995) and U.S. Pat. No. 6,613,340 (2003) are multi-step, low yielding and non eco-friendly. They involve use of p-toluene sulphonyl chloride as well as halogenated solvents. Since the synthetic routes for alkyl tosylates described in these patents go via sulphonyl chloride, it necessitates use of an organic base. Thus, use of solvents, generation of by-products like salt of organic base-hydrochloride and the necessary purification steps that result in not only lower yield of isolated product but heavy load on effluent treatment. This can be easily eliminated by the new process described in the present invention. The process of the present invention is a simple one with quantitative conversions and does not generate effluents and hence environment friendly. This is achieved through designing this novel process that avoids solvents including halogenated ones, reagents like p-toluene sulphonyl chloride and organic bases.

The successful application of this methodology has been demonstrated by converting water-soluble bis halides of cinnamidoalkylamine to water insoluble tosylates. This is again significant in view of the fact that water insoluble quaternary UV-absorbers are more substantive than water-soluble ones [Soap, Perfumery & Cosmetics, 28–30, August, 2002].

EXAMPLES

The invention will now be illustrated with the help of examples. The examples are by way of illustrations only and in no way restrict the scope of invention.

Alkyl halides were obtained from Henkel. p-Toluene sulphonic acid was obtained from Aldrich. p-Methoxy cinnamidopropyldimethylamine and p-N,N-dimethylamino benzamidopropyl dimethylamine were synthesised as per literature procedures [U.S. Pat. No. 5,427,773 (1995), U.S. Pat. No. 6,613,340 (2003)]. 1,1'-oxy bis[(4-methoxy cinnamidopropyl dimethyl ammonio) ethane] dichloride was prepared according to U.S. Pat. No. 6,426,435 (2002).

Example I

Process for Preparation p-methoxy cinnamidopropyldimethyllauryl ammonium tosylate (The compound of Formula I, wherein, ArCO=p-methoxy cinnamoyl; $R_1$=H; $R_2$, $R_3$=$CH_3$; n=3; $R_4$=—$C_{12}H_{25}$).

a) Preparation of p-methoxy cinnamidopropyldimethyllauryl ammonium chloride A mixture of lauryl chloride (7.8 g, 38.17 mmol) and p-methoxy cinnamidopropyldimethyl amine (10.0 g, 38.17 mmol) was stirred under blanket of nitrogen at 110° C. for 20 hours. The progress of reaction was monitored by estimation of unquaternised amine. Estimated chloride ion and free amidoamine was found to be 7.6% and 0.12% respectively. On cooling, the reaction yielded the quaternary ammonium compound (17.78 g, 99.9%) as pale yellow solid.

b) Preparation of p-methoxy cinnamidopropyldimethyllauryl ammonium tosylate p-Methoxy cinnamidopropyldimethyllauryl ammonium chloride (17.78 g, 38.11 mmol) was dissolved in water (60 ml) to make 30% solution. To this stirred solution, sodium p-toluene sulphonate (7.4 g, 38.14 mmol) was added and the separated pale yellow coloured solid was subsequently washed with water, filtered and dried to yield the corresponding tosylate (22.9 g, 99.83%) as off-white solid, m.p. 128–130° C. Chloride ion was totally absent in the product.

IR ($CH_2Cl_2$): 3465, 3286, 3052, 2920, 1659, 1617 $cm^{-1}$.

$^1$H NMR ($CDCl_3$, 300 MHz): δ 0.87 (3H, t, J=6.3 Hz), 1.18 (18H, broad signal), 1.58 (2H, unresolved multiplet), 2.10 (2H, unresolved multiplet), 2.32 (3H, singlet, methyl of tosyl), 3.13 (6H, singlet, two methyl on nitrogen), 3.20 (2H, unresolved multiplet), 3.45 (2H, unresolved multiplet), 3.68 (2H, unresolved multiplet), 3.78 (3H, singlet, $OCH_3$), 6.52 (1H, d, J=15.6 Hz), 6.76 (2H, d, J=8.4 Hz), 7.14 (2H, d, J=6.0 Hz), 7.31 (2H, d, J=8.6 Hz), 7.48 (1H, d, J=15.6 Hz), 7.78 (2H, d, J=7.8 Hz).

$^{13}$C NMR (125 MHz, $CDCl_3$): δ 14.10, 21.27, 22.69, 26.35, 29.23, 29.34, 29.51, 29.64, 31.93, 36.38, 50.67, 55.24, 62.47, 64.24, 114.10, 119.43, 125.83, 127.92, 128.89, 129.47, 139.56, 143.87, 160.67, & 167.25.

The molar extinction coefficient, ε was found to be 25,000 at λmax 310 nm in methanol. The final compound was analysed on HPLC using ion-pairing technique. The mobile phase employed for ion-pairing comprised of 0.1 M octane sulphonic acid in aqueous methanol (80:30). Reversed phase column Chromspher C8 was used with mobile phase flow rate of 1.0 ml/min. The detection was done at 280 nm. The purity of final compound from this analysis was found to be 99.9%.

The spectral and chromatographic data were in total agreement with the reported values.

Example II

Process for Preparation of p-N,N-dimethylamino benzamidopropyldimethyl lauryl ammonium tosylate (The compound of Formula I, wherein, ArCO=p-N,N-dimethylamino benzoyl; $R_1$=H; $R_2$, $R_3$=$CH_3$; n=3; $R_4$=—$C_{12}H_{25}$).

a) Preparation of p-N,N-dimethylamino benzamidopropyl dimethyl lauryl ammonium chloride A mixture of lauryl chloride (2.46 g, 12.05 mmol) and p-N,N-dimethylamino benzamido propyldimethyl amine (3.0 g, 12.05 mmol) was stirred under blanket of nitrogen at 110° C. for 20 hours. The progress of reaction was monitored by estimation of unquaternised amine as well as chloride ion. Estimated chloride ion and free amidoamine was found to be 7.83% and 0.15% respectively. On cooling, the reaction yielded the quaternary ammonium compound (5.455 g, 99.9%) as pale yellow solid.

b) Preparation of p-N,N-dimethylamino benzamidopropyl dimethyl lauryl ammonium chloride tosylate p-N,N-Dimethylamino benzamidopropyldimethyllauryl ammonium chloride (5.455 g, 12.03 mmol) was dissolved in water to make 30% solution. To this stirred solution, sodium p-toluene sulphonate (2.34 g, 12.06 mmol) was added and the separated pale yellow coloured solid was subsequently washed with water, filtered and dried to yield the corresponding tosylate (7.08 g, 99.93%) as pale yellow coloured solid. Chloride ion was totally absent in the product.

The spectral data (UV, IR and $^1$H NMR) was found to be identical with the one obtained by literature route. Reversed phase HPLC showed it to be 99.9% pure.

Example III

Process for Preparation of 1,1'-oxy bis[(4-methoxy cinnamidopropyl dimethyl ammonio) ethane]ditosylate (The compound of Formula VI, wherein, ArCO=p-methoxy cinnamoyl; $R_1$=H; $R_2$, $R_3$=$CH_3$; n=3; m=1).

Isopropanolic solution of 1,1'-oxy bis[(4-methoxy cinnamidopropyl dimethyl ammonio) ethane] dichloride (20.0 g, 19.5 mmol) was stirred with sodium p-toluene sulphonic acid (7.66 g, 39.5 mmol) at 80° C. for 8 hours. The sodium chloride separated was filtered to give isopropanolic solution of bis tosylate. IPA removal gave bis quaternary tosylate as sticky solid that was found to be water insoluble. It has very good solubility in alcohols and glycols.

$^1$H NMR of dried bis tosylate confirmed the structure. The filtered sodium chloride was found to be quantitative.

What is claimed is:

1. A process for preparing quaternary ammonium tosylates of Formula VI,

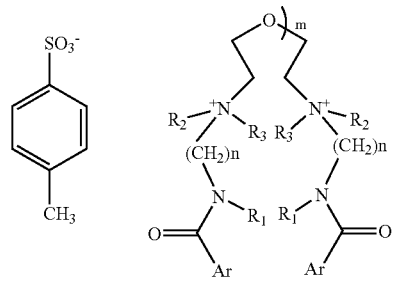 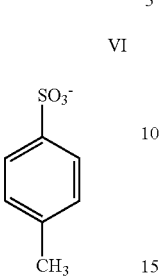

where: each ArCO is independently p-N,N-dimethylamino benzoyl or p-methoxy cinnamoyl;

$R_1$ is selected from H or alkyl groups containing from 1 to 6 carbon atoms;

$R_2$ and $R_3$ are independently selected from alkyl groups containing from 1 to 12 carbon atoms;

n is an integer having values from 1 to 6; and m is an integer having values from 1 to 10; the process comprising:

reacting a compound of Formula V with sodium p-toluene sulphonate, the respective substituents ArCO, $R_1$, $R_2$, $R_3$, n and m of Formula V, being as defined for the compounds of Formula VI in this claim:

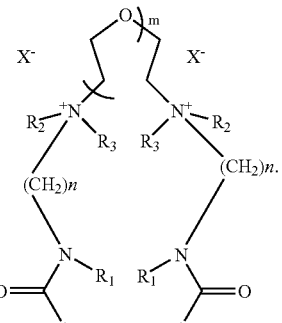

2. A water insoluble quaternary ammonium bis tosylate of Formula VI;

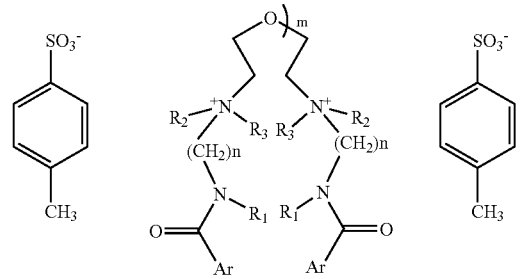

where: each ArCO is independently p-N,N-dimethylamino benzoyl or p-methoxy cinnamoyl;

$R_1$ is selected from H or alkyl groups containing from 1 to 6 carbon atoms, $R_2$ and $R_3$ are independently selected from alkyl groups containing from 1 to 12 carbon atoms;

n is an integer having values from 1 to 6; and m is an integer having values from 1 to 10.

* * * * *